United States Patent [19]

Moet et al.

[11] Patent Number: 5,396,804
[45] Date of Patent: Mar. 14, 1995

[54] APPARATUS AND METHOD FOR FORCE-CONTROLLED FATIGUE TESTING

[75] Inventors: Abdelsamie Moet, Cleveland Heights; Hamdy Alaa, Cleveland; Wassim Hafez, Cleveland Heights, all of Ohio

[73] Assignee: Gas Research Institute, Chicago, Ill.

[21] Appl. No.: 134,939

[22] Filed: Oct. 12, 1993

[51] Int. Cl.$^6$ .......................... G01N 3/06; G01D 1/16
[52] U.S. Cl. .......................... 73/788; 73/787; 73/789; 73/811
[58] Field of Search .................. 73/788, 787, 789, 811

[56] References Cited

U.S. PATENT DOCUMENTS

| | | | |
|---|---|---|---|
| 2,685,794 | 1/1951 | Hall et al. | 73/788 |
| 3,209,584 | 10/1965 | Lathrop | 73/797 |
| 3,589,175 | 6/1971 | Bock et al. | 73/791 |
| 3,621,711 | 11/1971 | Griffith et al. | 73/797 |
| 3,793,880 | 2/1974 | Sugi et al. | 73/797 |
| 4,019,375 | 4/1977 | Ellis et al. | 73/583 |
| 4,056,973 | 11/1977 | Prevorsek et al. | 73/789 |
| 4,544,154 | 10/1985 | Ariel | 272/189 |
| 4,559,812 | 12/1985 | Kitchen | 73/54.32 |
| 4,869,111 | 9/1989 | Ohya et al. | 73/811 |
| 4,901,580 | 2/1990 | Potts | 73/788 |
| 5,079,956 | 1/1992 | Burhin et al. | 73/846 |
| 5,154,085 | 10/1992 | Takeda | 73/811 |

FOREIGN PATENT DOCUMENTS

| | | | |
|---|---|---|---|
| 0267643 | 11/1987 | Japan | 73/788 |
| 0163254 | 7/1988 | Japan | 73/788 |
| 0201243 | 8/1990 | Japan | 73/788 |
| 4301741 | 10/1992 | Japan | 73/788 |

OTHER PUBLICATIONS

"Marks' Standard Handbook for Mechanical Engineers", Theodore Baumeister, copyright 1978, p. 16–8.

Primary Examiner—Hezron E. Williams
Assistant Examiner—James M. Olsen
Attorney, Agent, or Firm—Speckman, Pauley & Fejer

[57] ABSTRACT

An apparatus and method for force-controlled fatigue testing of a specimen or material. A driver is used to generate a load force which is applied to the test specimen. Physical property changes of the test specimen are measured over time and a feedback signal is generated as a function of the measured physical property changes. A motion command signal is computed as a function of the feedback signal. A computer processes the feedback signal and emits the motion command signal to an actuator. The driver responds to the motion command signal and maintains the load force at an approximately constant magnitude during the physical property changes of the test specimen.

11 Claims, 2 Drawing Sheets

APPARATUS AND METHOD FOR FORCE-CONTROLLED FATIGUE TESTING

BACKGROUND OF THE INVENTION

1. Field of the Invention

This invention relates to an relates to an apparatus and method for controlled fatigue testing of a specimen wherein a magnitude of a load force applied to the specimen is varied over time so that the load force upon the test material is maintained constant during physical property changes of the test material.

2. Description of Prior Art

It is crucial to be able to create accurate and stable loading conditions during fatigue testing of a specimen or sample material. According to conventional apparatuses and methods, arbitrary force profiles cannot be generated without elaborate tuning of a force controller designed for a specific class of materials, which defeats the purpose of the testing activity since such conventional apparatuses and methods require prior knowledge of the physical properties of the specimen or material. With such conventional apparatuses and methods, even if they could be properly tuned, it would be very difficult to compensate for slow dynamic changes in the physical properties of the specimen, such as those caused by geometric deformations and propagation of cracks, which can lead to undetected instability of loading conditions.

It is important to distinguish between the control mechanisms of fatigue testing systems and those of other control systems, such as numerical controllers that are employed in machine tooling systems, temperature controllers, liquid level controllers and the like. In such other control systems, the control input variable, such as pulse frequency, coil current or valve position, is independent of the controlled variable, such as position, temperature and liquid level. However, in fatigue testing systems, the control variable, such as displacement, and the controlled variable, such as the load, interact through the unknown test specimen. The displacement variable plays a dual role, a control variable and a response variable of the test. Thus, the load becomes a test signal that directly depends upon the physical properties of the test specimen or other test material.

In some conventional fatigue testing equipment controlled variables other than displacement are used to control the load on the test specimen, which limits the force profiles that can be generated and often results in overheating of drive motors. Also, such conventional fatigue testing apparatuses use torque motors which provide relatively low positioning resolution, due to analog control circuits, and thus less stable load profiles.

U.S. Pat. No. 5,154,085 discloses a tension type dynamic viscoelasticity measuring apparatus which applies a prescribed force to a viscoelastic test material. Over time, due to molecular relaxation effects, the applied force diminishes. In order to correct for an anticipated relaxation-induced or time-dependent reduction in the force acting on the test specimen, the apparatus taught by the '085 patent exerts additional displacement or extension at a magnitude which is computed as a function of time. The control system taught by the '085 patent is considered to be open loop with respect to the tensile force. Since the apparatus taught by the '085 patent does not measure the actual force acting on the test specimen, adjustments in the specimen displacement tend to promote relaxation-induced force reductions. According to the apparatus of the '085 patent, the accuracy of the actual force magnitude relies on the predictive power of the time function.

It is well known that the intensity of stressed-relaxation of a polymer depends upon its molecular structure and its physical state. The number of common types of polymers and their corresponding physical states are so large that a preset time function cannot account for such variance.

The displacement-based feedback control taught by the '085 patent cannot be used to generate constant load magnitude which is essential for fatigue testing. The load prescribed by the moving mechanism taught by the '085 patent diminishes not only due to stress relaxation, a molecular process, but also due to cracks and other plastic deformation processes which cannot be compensated for by any known time function. The force acting on a polymer specimen under fatigue testing usually diminishes due to dimensional changes of the specimen, such as thinning, which cannot be compensated for through a time function. Fatigue testing involves complex specimen geometries, such as a plastic pipe section or a fused joint, wherein actual response to the applied force must be measured and corrected in real time. Fatigue testing requires intermittent application of tensile force and/or compressive force, thus the motion mechanism and control taught by the '085 patent is ineffective.

SUMMARY OF THE INVENTION

It is one object of this invention to provide an apparatus and method for force-controlled fatigue testing of a specimen wherein a force feedback loop is used to continuously correct a difference between a desired and a measured force profile.

It is another object of this invention to provide an apparatus and method wherein physical property changes of the test specimen are measured over time and the load force applied to the test specimen is maintained at a constant magnitude, even during physical property changes of the test specimen.

It is another object of this invention to provide an apparatus and method which accommodates tension, compression and bending tests.

It is still another object of this invention to provide an apparatus and method which can be used for fatigue testing and fatigue crack propagation testing of plastics, metals, ceramics, composites, adhesives, and other natural materials in various loading modes for various geometries of the test specimens.

The above and other objects of this invention are accomplished with an apparatus that includes an actuator for applying the load force to the test specimen. Physical property changes of the specimen are measured over time and are used to generate a feedback signal as a function of the measured physical property change. A motion command signal is computed as a function of the feedback signal and a computer emits the motion command signal to the actuator. A driver of the actuator responds to the motion command signal and thus maintains the load force at an approximately constant magnitude, even during physical property changes of the test specimen.

The stability and accuracy of the apparatus and process according to this invention stem from an adaptive force control mechanism which automatically adjusts the stiffness of the control loop in order to match the slowly time-varying stiffness of the test specimen. It is an important aspect of this invention to adjust the load force applied to the test specimen in order to compensate for the dynamic changes in the stiffness of the test specimen and to accommodate for the wide ranges of materials being tested. Many fatigue tests are conducted over a relatively long time period, such as several weeks. The apparatus and method according to this invention incorporate stiffness control in lieu of indirect force control which is a function of the displacement that operates as the control variable.

The motion command signal or force control signal according to this invention is preferably computed using a recursive least square estimate of the stiffness of the test specimen and a difference between the desired and actual load profiles. Because the control computations are calculated in a background mode using hardware interrupts, the estimation time is minimized by exploiting special floating point functions of a microprocessor, which preferably allows about 2,000 samples per second.

The apparatus according to this invention preferably uses a high-precision stepper motor and driver which provide very accurate and stable behavior for all test signals up to approximately 1,000 lb. at 0.2 micron positioning resolution.

The force control system according to this invention provides consistent accuracy and stability for a wide range of test materials, without manual tuning of various parameters. The relatively small size, reduced noise levels and low cost of stepper motors and their drivers are an added benefit of the apparatus according to this invention, particularly when compared with torque motors and hydraulic actuators used in conventional apparatuses.

BRIEF DESCRIPTION OF THE DRAWINGS

The above-mentioned and other features and objects of this invention will be better understood from the following detailed description taken in conjunction with the drawings wherein.

DESCRIPTION OF PREFERRED EMBODIMENTS

Figures 1, 2:
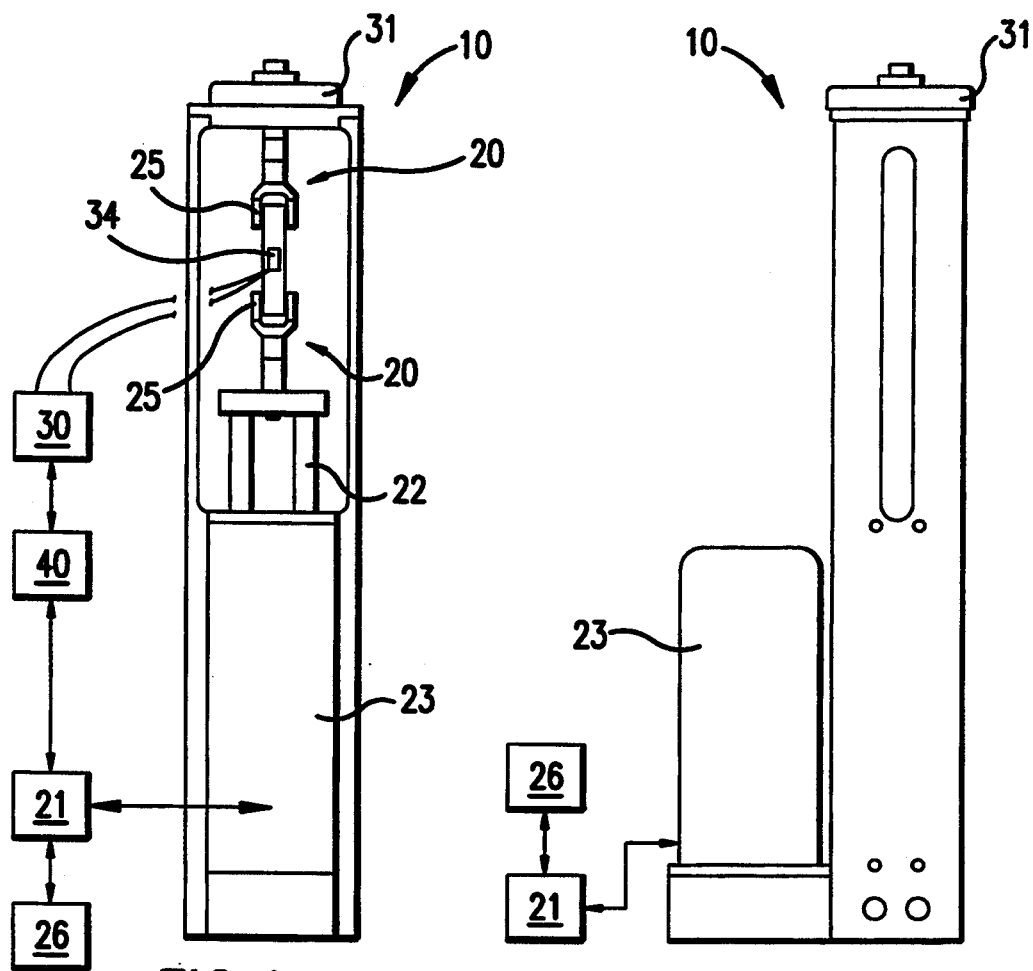
FIG. 1 is a diagrammatic front view of a force-controlled fatigue testing apparatus, according to one preferred embodiment of this invention.
FIG. 2 is a diagrammatic side view of the force-controlled fatigue testing apparatus, as shown in FIG. 1.
Figure 3:
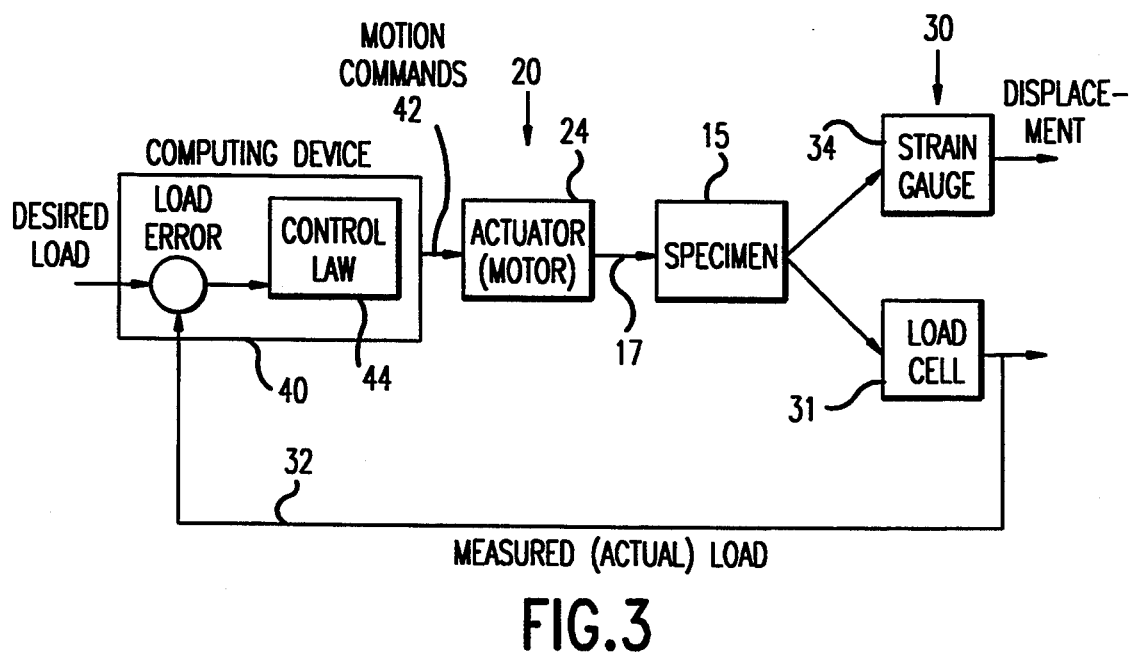
FIG. 3 is a block diagram of the force-controlled fatigue testing apparatus operating in a force feedback mode for generation of a test load, according to one preferred embodiment of this invention.
Figure 4:
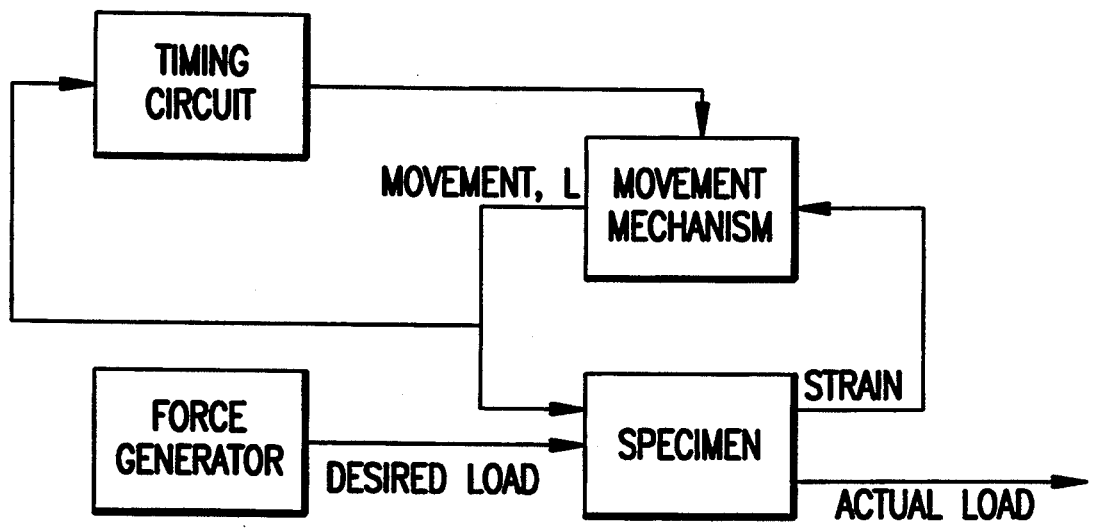
FIG. 4 is a block diagram of a conventional testing apparatus operating in an open loop mode for generation of a test load, as defined by the general state of the art.

Referring to FIGS. 1-3, force-controlled fatigue testing apparatus 10 according to one preferred embodiment of this invention comprises actuating means 20, measurement means 30, and computer means 40. Actuating means 20 are used to apply load force 17 to specimen 15. As shown in FIG. 1, actuating means 20 preferably comprise driver 21, stepper motor 23 and motion transfer mechanism 22, for generating load force 17. Stepper motor 23 is operatively coupled to motion transfer mechanism 22 by any suitable coupling known to those skilled in art.

In one preferred embodiment according to this invention, actuating means 20 comprise positioning means 25 for educing displacement changes upon specimen 15. It is apparent that positioning means 25 may comprise grips as shown in FIG. 1, mechanical claws or any other suitable element for holding or mounting specimen 15. Actuating means 20 may also comprise power electronic module 26. It is apparent that actuating means 20 may comprise other electronic, hydraulic and/or mechanical components known to those skilled in the art.

As shown in FIGS. 1 and 3, force-controlled fatigue testing apparatus 10 also comprises measurement means 30 for measuring a physical property change of specimen 15 as load force 17 is applied to specimen 15 over time. Measurement means 30 are also used to generate feedback signal 32 as a function of the measured physical property change of specimen 15. In one preferred embodiment according to this invention, measurement means 30 comprise strain gauge 34 which preferably emits a measurement signal to computer means 40. The measurement signal can represent the measured physical property change or changes of specimen 15. In another preferred embodiment according to this invention, measurement means 30 comprise load cell 31 which is used to detect load changes upon specimen 15. Computer means 40 are used to compute motion command signal 42 as a function of feedback signal 32. Computer means 40 emit motion command signal 42 to actuating means 20. In one preferred embodiment according to this invention, computer means 40 may comprise data acquisition means 44 for receiving and processing feedback signal 32. Computer means 40 may comprise an Intel TM 80387 co-processor, for example, which allows about 2000 samples per second and thus can minimize the estimation time.

Computer means 40 preferably derive motion command signal 42 in real time, as a function of a frequency and an magnitude of load force 17, wherein the frequency and the magnitude are necessary to continuously produce a reference force signal. Motion command signal 42 can be used to vary the magnitude, the frequency and/or a direction of load force 17 of driver 21, as a function of feedback signal 32. Computer means 40 preferably compute motion command signal 42 based on a difference between a measured load force 32 and a desired load force.

The mechanical and electrical connections between elements described in this specification can be accomplished with suitable connections apparent to those skilled in the art. The framework of force-controlled fatigue testing apparatus 10 can be constructed as shown in FIGS. 1 or 2, or can be constructed in any other suitable manner which would be apparent to those skilled in the art.

A method for operating force-controlled fatigue testing apparatus 10, according to one preferred embodiment of this invention, begins with applying load force 17 to specimen 15. One or more physical property changes of specimen 15 are measured over time, such as with strain gauge 34. Feedback signal 32 is generated as a function of each measured physical property change.

Motion command signal 42 is computed as a function of feedback signal 32. Motion command signal 42 is preferably emitted to and received by actuator 24. Actuator 24 is controlled to maintain load force 17 at an approximately constant magnitude during the physical property changes of specimen 15. In one preferred embodiment according to this invention, feedback signal 32 represents a measured actual load force which is applied to specimen 15.

The force feedback loop according to this invention enables continuous correction of any difference between the desired test load profile and the actual specimen load profile. Computer means 40 can change the frequency of the motion sequence command about 200 times per second, which involves changing the speed and possibly the direction of actuator 24 or stepper motor 23 every 5 milliseconds in order to eliminate any difference between the desired test load profile and the actual specimen load profile. In order to maintain stability of the control system of this invention over extended testing time periods, since a single fatigue test may require uninterrupted machine operation for several weeks as compared to several minutes with conventional dynamic mechanical fatigue testing apparatuses, the feedback loop according to this invention must be continuously adjusted to compensate for significant changes in the physical state of test specimen 15.

The apparatus and method according to this invention can be used to test the resistance of a material to large scale deformation due to relatively large load magnitudes applied in cycles. The apparatus and method according to this invention can be used to determine the number of cycles to failure and the rate of crack propagation under constant fatigue load magnitudes.

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention.

What is claimed is:

1. An apparatus for force-controlled fatigue testing of a specimen, the apparatus comprising:
    actuating means for applying a load force to the specimen, said actuating means comprising a driver for generating said load force;
    measurement means for measuring an actual load force applied to the specimen and a physical property change of the specimen over time and for generating a physical property change feedback signal as a function of said measured physical property change and for generating an actual load force feedback signal as a function of said measured actual load force;
    computer means for estimating a stiffness of the specimen as a function of said physical property change feedback signal and said actual load force feedback signal, and computing a motion command signal as a function of said actual load force feedback signal, a desired load force profile, and a time-variable stiffness of the specimen, said computer means emitting said motion command signal to said actuating means; and
    said driver responding to said motion command signal and maintaining said load force at an approximately constant magnitude during said physical property change of the specimen.

2. A force-controlled fatigue testing apparatus according to claim 1 wherein said actuating means comprise an actuator having positioning means for inducing displacement changes of the specimen.

3. A force-controlled fatigue testing apparatus according to claim 1 further comprising a stepper motor operatively coupled to said driver.

4. A force-controlled fatigue testing apparatus according to claim 1 wherein said actuating means comprise a power electronic module in electrical communication with said driver.

5. A force-controlled fatigue testing apparatus according to claim 1 wherein said measurement means comprise a strain gauge emitting a measurement signal to said computer means, said measurement signal representing said measured physical property change of the specimen.

6. A force-controlled fatigue testing apparatus according to claim 1 wherein said measurement means comprise a load cell detecting load changes on the specimen.

7. A force-controlled fatigue testing apparatus according to claim 1 wherein said computer means comprise data acquisition means for receiving and processing said feedback signal.

8. A force-controlled fatigue testing apparatus according to claim 1 wherein said computer means derive in real time said motion command signal as a function of a frequency and an magnitude of said load force wherein said frequency and said magnitude are necessary to continuously produce a reference force signal.

9. A force-controlled fatigue testing apparatus according to claim 1 wherein said motion command signal is used to vary at least one of magnitude, a frequency and a direction of said load force of said driver.

10. A force-controlled fatigue testing apparatus according to claim 1 wherein said computer means computes said motion command signal which represents a difference between said measured actual load force on the specimen and a delivered load force to the specimen.

11. A method for force-controlled fatigue testing of a specimen, the method comprising the steps of:
    (a) providing a computer with a desired load force profile;
    (b) applying a load force to the specimen according to said desired load force profile;
    (c) measuring an actual load force applied to the specimen over time;
    (d) measuring a physical property change of the specimen over time;
    (e) generating a physical property change feedback signal as a function of said measured physical property change;
    (f) generating an actual load force feedback signal as a function of said measured actual load force;
    (g) estimating a stiffness of the specimen as a function of said physical property change feedback signal and said actual load force feedback signal;
    (h) computing a motion command signal as a function of said actual load force feedback signal, said desired load force profile and a time-variable stiffness of the specimen;
    (i) emitting said motion command signal to an actuator; and
    (j) controlling said actuator to maintain said load force at an approximately constant magnitude during said physical property change of the specimen.

* * * * *